United States Patent
Bolling (12)

(10) Patent No.: US 6,200,260 B1
(45) Date of Patent: Mar. 13, 2001

(54) IMPLANTABLE HEART ASSIST SYSTEM

(75) Inventor: Steven F. Bolling, Costa Mesa, CA (US)

(73) Assignee: Fore Flow Corporation, Forest, CA (US)

( * ) Notice: Subject to any disclaimer, the term of this patent is extended or adjusted under 35 U.S.C. 154(b) by 0 days.

(21) Appl. No.: 09/166,005

(22) Filed: Oct. 2, 1998

Related U.S. Application Data (60) Provisional application No. 60/061,434, filed on Oct. 9, 1997.

(51) Int. Cl.$^7$ ............................. A61M 1/10; A61H 31/00
(52) U.S. Cl. ................................................ 600/16; 600/17
(58) Field of Search .......................................... 600/16, 17

(56) References Cited

U.S. PATENT DOCUMENTS

| | | |
|---|---|---|
| 2,935,068 | 5/1960 | Donaldson . |
| 3,017,885 * | 1/1962 | Robicsek ................................ 600/16 |
| 3,592,184 | 7/1971 | Watkins et al. . |
| 3,692,018 | 9/1972 | Goetz et al. . |
| 3,835,864 | 9/1974 | Rasor et al. . |
| 3,885,251 | 5/1975 | Pedrosa . |
| 3,939,820 | 2/1976 | Grayzel . |
| 3,964,479 | 6/1976 | Boag et al. . |
| 4,004,299 | 1/1977 | Runge . |
| 4,034,742 | 7/1977 | Thoma . |
| 4,047,849 | 9/1977 | Clay . |
| 4,077,394 | 3/1978 | McCurdy . |
| 4,080,958 * | 3/1978 | Bregman et al. ..................... 128/1 D |
| 4,135,496 | 1/1979 | Chazov et al. . |
| 4,143,616 | 3/1979 | Bible . |
| 4,154,227 | 5/1979 | Krause et al. . |
| 4,167,046 | 9/1979 | Portner et al. . |
| 4,240,409 | 12/1980 | Robinson et al. . |

(List continued on next page.)

FOREIGN PATENT DOCUMENTS

| | | |
|---|---|---|
| 0232074 | 1/1987 | (EP) . |
| 1303165 A2 | 1/1985 | (RU) .............................. A61M/1/10 |

OTHER PUBLICATIONS

JAMA, Jan. 8, 1968, vol. 203, No. 2, Initial Clinical Experience With Intra–aortic Balloon Pumping in Cardiogenic Shock, pp 113–118.
Article: Magnetically Suspended Vad, pp M361, 363, 364.
Article: Mechanical Auxiliary Ventricle, pp M345–355.
Article: A Mechanical Auxiliar Ventricle, pp M340–344.
Patent Server; Patent Search Reports: 15 pp total.
Patent Server; Search Results; 30 pp total.
Article: Effect of Stationary Guiding Vanes on Improvement of the Washout Behind the Rotor in Centrifugal Blood Pumps; pp M220–M224.
Article: An Implantable Seal–less Centrifugal Pump with Integrated Double–Disk Motor; pp 639–642.

(List continued on next page.)

*Primary Examiner*—Carl H. Layno
(74) *Attorney, Agent, or Firm*—Knobbe, Martens, Olson & Bear, LLP (57) ABSTRACT

An extracardiac pumping system for supplementing the circulation of blood through a patient without any component thereof being connected to the patient's heart, and method of using same. The extracardiac system comprises a pump implanted subcutaneously at or about the patient's groin in a minimally-invasive procedure, wherein the pump is powered by a battery, and means for charging the battery extracorporeally, wherein the pump draws blood through an inflow conduit fluidly coupled to the patient's femoral artery via a subcutaneous anastomosis connection, and discharges blood through an outflow conduit fluidly coupled to a peripheral artery that stems from the patient's aortic arch via a subcutaneous anastomosis connection. The pump may be operated continuously or in a pulsatile fashion, synchronous with the patient's heart, thereby potentially reducing the pumping load on the heart.

25 Claims, 6 Drawing Sheets

U.S. PATENT DOCUMENTS

| | | |
|---|---|---|
| 4,302,854 | 12/1981 | Runge . |
| 4,384,829 | 5/1983 | Conley et al. . |
| 4,407,271 | 10/1983 | Schiff . |
| 4,457,673 | 7/1984 | Conley et al. . |
| 4,522,195 | 6/1985 | Schiff . |
| 4,546,759 | 10/1985 | Solar . |
| 4,552,552 | 11/1985 | Polaschegg et al. . |
| 4,573,997 | 3/1986 | Wisman et al. . |
| 4,611,578 | 9/1986 | Helmes . |
| 4,625,712 | 12/1986 | Wampler . |
| 4,666,443 | 5/1987 | Portner . |
| 4,685,446 | 8/1987 | Choy . |
| 4,688,998 | 8/1987 | Olsen et al. . |
| 4,690,134 | 9/1987 | Snyders . |
| 4,697,574 | 10/1987 | Karcher et al. . |
| 4,719,921 | 1/1988 | Chirife . |
| 4,756,302 | 7/1988 | Portner et al. . |
| 4,759,760 | 7/1988 | Snapp, Jr. . |
| 4,771,765 | 9/1988 | Choy et al. . |
| 4,822,357 | 4/1989 | Forster et al. . |
| 4,838,889 | 6/1989 | Kolff . |
| 4,861,330 | 8/1989 | Voss . |
| 4,872,874 | 10/1989 | Taheri . |
| 4,883,462 | 11/1989 | Williamson et al. . |
| 4,895,150 | 1/1990 | Isaacson et al. . |
| 4,902,272 | 2/1990 | Milder et al. . |
| 4,902,273 | 2/1990 | Choy et al. . |
| 4,906,229 | 3/1990 | Wampler . |
| 4,908,012 | 3/1990 | Moise et al. . |
| 4,927,407 | 5/1990 | Dorman . |
| 4,957,504 | 9/1990 | Chardack . |
| 4,968,293 | 11/1990 | Nelson . |
| 4,994,078 | 2/1991 | Jarvik . |
| 4,995,856 | 2/1991 | Heindl et al. . |
| 4,995,857 | 2/1991 | Arnold . |
| 5,020,516 | 6/1991 | Biondi et al. . |
| 5,059,167 * | 10/1991 | Lundquist et al. ............... 600/16 |
| 5,069,662 | 12/1991 | Bodden . |
| 5,089,017 | 2/1992 | Young et al. . |
| 5,092,844 | 3/1992 | Schwartz et al. . |
| 5,098,370 | 3/1992 | Rahat et al. . |
| 5,116,564 | 5/1992 | Jansen et al. . |
| 5,129,878 | 7/1992 | Takano et al. . |
| 5,131,905 | 7/1992 | Grooters . |
| 5,133,744 | 7/1992 | Ramos Martinez . |
| 5,147,281 * | 9/1992 | Thornton et al. ............... 600/16 |
| 5,147,388 | 9/1992 | Yamazaki . |
| 5,169,378 | 12/1992 | Figuera . |
| 5,169,379 | 12/1992 | Freed et al. . |
| 5,171,207 | 12/1992 | Whalen . |
| 5,176,619 | 1/1993 | Segalowitz . |
| 5,211,659 | 5/1993 | Strimling et al. . |
| 5,263,978 | 11/1993 | Kaufmann et al. . |
| 5,267,940 | 12/1993 | Moulder . |
| 5,273,518 | 12/1993 | Lee et al. . |
| 5,300,113 | 4/1994 | Arpesella et al. . |
| 5,332,403 | 7/1994 | Kolff . |
| 5,346,458 | 9/1994 | Affeld . |
| 5,352,180 | 10/1994 | Candelon et al. . |
| 5,374,239 | 12/1994 | Mischenko . |
| 5,376,113 | 12/1994 | Jansen et al. . |
| 5,429,584 | 7/1995 | Chiu . |
| 5,453,076 | 9/1995 | Kiyota et al. . |
| 5,503,615 | 4/1996 | Goldstein . |
| 5,511,958 | 4/1996 | Chen et al. . |
| 5,562,595 | 10/1996 | Neisz . |
| 5,584,804 | 12/1996 | Klatz et al. . |
| 5,746,575 | 5/1998 | Westphal et al. . |

OTHER PUBLICATIONS

Article : Flow Measurement at the Pump Head of Centrifugal Pumps: Comparsion of Ultrasonic Transit Time and Ultrasonic Doppler Systems; pp 808–815.

Patent Server; Search Reports; 32 pp total.

Article: George J. Magovern, Jr. MD, Use of Biomedicus Pump in Postoperative Circulatory Support; 6 pp total.

Article: Bruce J. Shook, MS Eng., The Abiomed BVS 5000 Biventricular Support System, 6 pp total.

Article: Valluvan Jeevanandam, MD, et al., TCI Heartmate Left Ventricular Assist System: Results with Bridge to Transplant and Chronic Support, 5 pp total.

Article: O.H. Frazier, MD, Long–Term Ventricular Support with the Heartmate in Patients Undergoing Bridge–to–Transplant Operations; 3 pp total.

Article: Narayanan Ramasamy, Phd, et al., Novacor LVAS: Results with Bridge to Transplant and Chronic Support; 3 pp total.

Article: Report W. Emery, MD et al., Uses of Mechanical Circulatory Assist Devices at the Minneapolis Heart Institute; 5 pp total.

Article: Lawrence R. McBride, MD et al., Anticoagulation in Patients with Ventricular Assist Devices; 1 pg.

Article: Roque Pifarre, MD et al., Bridge to Transplantation with the Total Articical Heart: The Loyal Experince, 5 pp total.

Article: Pratap S. Khanwilkar, MS, MBA et al., Future Prospects for a totally Implantable Artificial Heart; 8 pp total.

Article: Concepts in the Application of Pneumatic Ventricular Assist Devices for Ischemic Myocardial Injury; pp 162–168.

Article: Long–Term Left Ventricular Assist Device Use Before Transplantation; pp M530–M534.

Article: In Vitro Characterization of a Magnetically Suspended Continuous Flow Ventricular Assist Device; pp M359–M360.

Article: Estimation of Left Ventricular Function in Patients With a Left Venticular Assist Device; M544–551.

Article: The Sternotomy Hemopump, A second Generation Intraarterial Ventricular Assist Device. PP M218–220, 223.

Article: Transarterial Closed–Chest Left Ventricular (TaCLV) Bypass. pp 386–390.

Article: First Clinical Application of Transarterial Closed–Chest Left Ventricular (TaCLV) Bypass, pp 386–391.

Article: Implnatable Left Ventricular Assist Device. pp 1522–1533.

Article: Effects of Partial and Complete Unloading of the Failing Left ventricle by Transarterial Left Heart Bypass. pp 865–872.

Article: "Long Term Follow Up of Survivors of Postcardiotomy Circulatory Support"; Author —Ruzevich, et al.,; 4535, A.S.A.I.O. Transactions 34 (1988) Apr.–Jun., No. 2, Hagerstown, MD, USA; pp 116–124.

Article: "Hemodynamic Effects of the Concomitant Use of Intra–Aoritic Balloon Pumping and Venoarterial Bypass without Oxygenation in Cardigenic Shock", Author —Takamoto et al.; Intra–Aortic Pumping & Venoraterial Bypass, vol. 19, No. 6; pp 938–945.

Article: "Mechanical Cardiopulmonary Support During Arteriography and Surgical Correction of Coronary Insufficiency Producing Myocardial Infarction With Cardiogenic Shock"; Author —Carlson et al.; Journal of the Association for the Advancement of Medical Instrumentation, vol. 6, No. 3 May–Jun. 1972; pp 244–248.

* cited by examiner

IMPLANTABLE HEART ASSIST SYSTEM

RELATED APPLICATIONS

This is based upon a provisional application filed Oct. 9, 1997, U.S. Provisional Application Serial No. 60/061,434, which is incorporated herein in its entirety by reference.

FIELD OF THE INVENTION

The present invention relates generally to a system for assisting the heart and, in particular, to an extracardiac pumping system and a method for supplementing the circulation of blood through the patient using a minimally invasive procedure.

BACKGROUND OF THE INVENTION

During the last decade, congestive heart failure (CHF) has burgeoned into the most important public health problem in cardiovascular medicine. As reported in Gilum, R. F., *Epidemiology of Heart Failure in the U.S.,* 126 Am. Heart J. 1042 (1993), four hundred thousand (400,000) new cases of CHF are diagnosed in the United States annually. The disorder is said to affect nearly 5 million people in this country and close to 20 million people worldwide. The number of hospitalizations for CHF has increased more than three fold in the last 15 years. Unfortunately, nearly 250,000 patients die of heart failure annually. According to the Framingham Heart Study, the 5-year mortality rate for patients with congestive heart failure was 75 per cent in men and 62 per cent in women (Ho, K. K. L., Anderson, K. M., Kannel, W. B., et al., *Survival After the Onset of Congestive Heart Failure in Framingham Heart Study Subject,* 88 Circulation 107 (1993)). This disorder represents the most common discharge diagnosis for patients over 65 years of age. Although the incidence of most cardiovascular disorders has decreased over the past 10 to 20 years, the incidence and prevalence of congestive heart failure has increased at a dramatic rate. This number will increase as patients who would normally die of an acute myocardial infarction (heart attack) survive, and as the population ages.

CHF manifests itself primarily by exertional dyspnea (difficult or labored breathing) and fatigue. Three paradigms are used to describe the causes and therapy of CHF. The first views this condition in terms of altered pump function and abnormal circulatory dynamics. Other models describe it largely in terms of altered myocardial cellular performance or of altered gene expression in the cells of the atrophied heart. In its broadest sense, CHF can be defined as the inability of the heart to pump blood throughout the body at the rate needed to maintain adequate blood flow, and many of the normal functions of the body.

Figure 1:
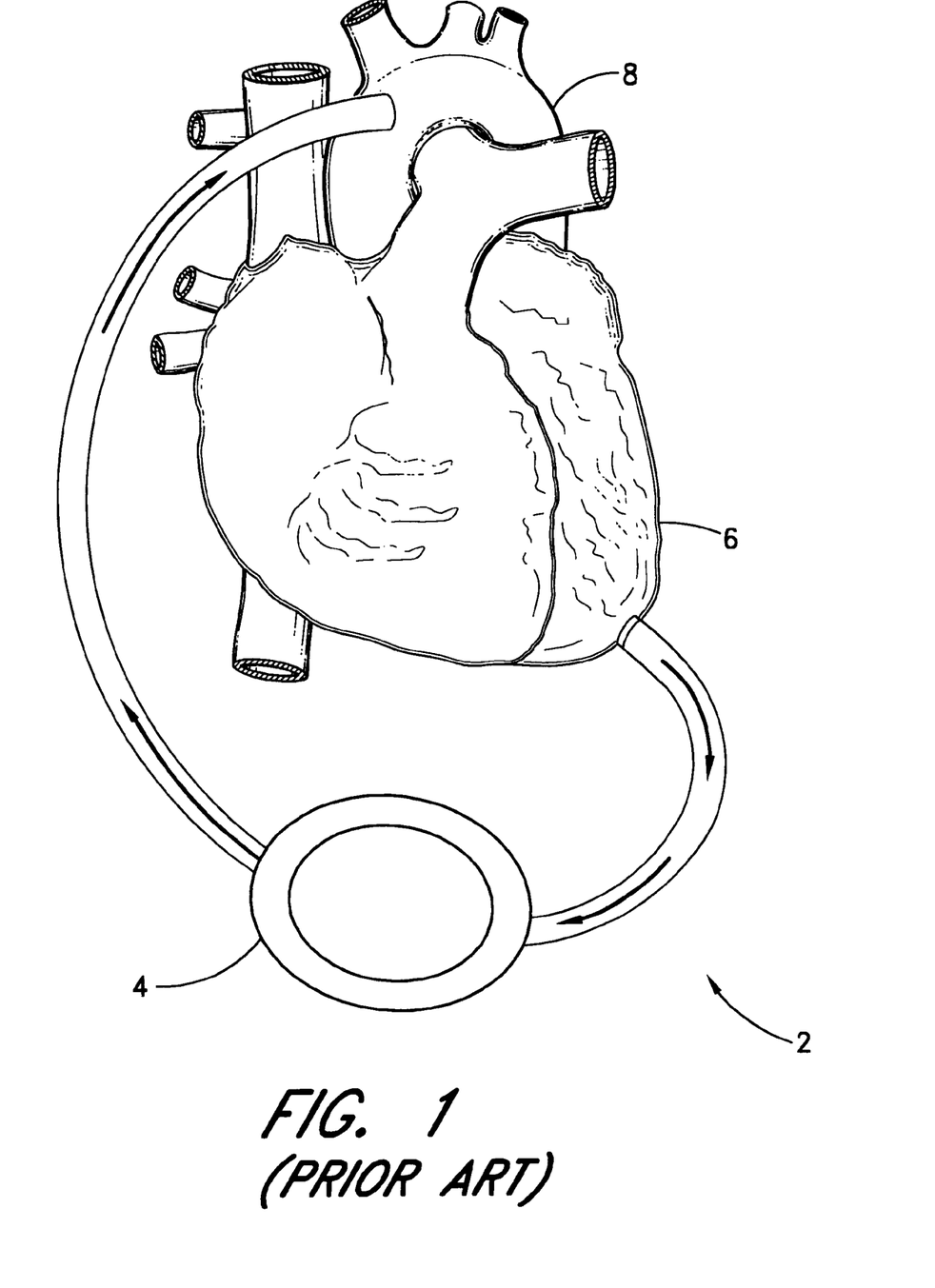
FIG. 1 is a schematic view of a cardiac assist device, known as a left ventricular assist device, showing a bypass from the apex of the left ventricle to the aortic arch.

To address CHF, many types of cardiac assist devices have been developed. A cardiac or circulatory assist device is one that aids the failing heart by increasing its pumping function or by allowing it a certain amount of rest to recover its pumping function. Because congestive heart failure may be chronic or acute, different categories of heart assist devices exist. Short of a heart transplant, at least two types of chronic heart assist systems have been developed. One type employs a full or partial prosthetic connected between the heart and the aorta, one example of which is commonly referred to as a LVAD—Left Ventricular Assist Device. With reference to FIG. 1 herein, one example of a LVAD 2 is shown. The LVAD comprises a pump and associated valves 4 that draws blood directly from the apex of the left ventricle 6 and directs the blood to the aortic arch 8, bypassing the aortic valve. In this application, the left ventricle stops functioning and does not contract or expand. The left ventricle becomes, in effect, an extension of the left atrium, with the LVAD 2 taking over for the left ventricle. The ventricle, thus, becomes a low-pressure chamber. Because the intent is to take over for the left ventricle, the LVAD operates by pumping blood at cardiac rates. With an LVAD, oxygenated blood circulation is established sufficient to satisfy the demand of the patient's organs.

Another type of chronic heart assist system is shown in U.S. Pat. No. 5,267,940 to Moulder. Moulder describes a pump implanted into the proximal descending aorta to assist in the circulation of blood through the aorta.

In addressing acute CHF, two types of heart assist devices have been used. One is counterpulsatory in nature and is exemplified by an intra-aortic balloon pump (IABP). With an IABP, the balloon is collapsed during isovolumic contraction, providing a reduced pressure against which the heart must pump blood, thereby reducing the load on the heart during systole. The balloon is then expanded, forcing blood omnidirectionally through the arterial system. Another example of this first type employs one or more collapsible chambers in which blood flows passively into the chamber during systole, as is shown in U.S. Pat. No. 4,240,409 to Robinson et al. The chamber is then collapsed and the blood forcibly returned to the aorta. These devices simulate a chamber of the heart and depend upon an inflatable bladder to effectuate pumping action, requiring an external pneumatic driver.

A second type of acute assist device utilizes an extracorporeal pump, such as the Biomedicus centrifugal pump, to direct blood through the patient while surgery is performed on the heart. In one example, described in U.S. Pat. No. 4,968,293 to Nelson, the heart assist system employs a centrifugal pump in which the muscle of the patient is mounted to add pulsatility to the blood flow. The Nelson device is used to bypass a portion of the descending aorta.

Another device, shown in U.S. Pat. No. 4,080,958 to Bregman et al., utilizes an inflatable and collapsible bladder to assist in blood perfusion during heart trauma and is intended to supplement a conventional heart-lung machine by imparting pulsatile actuation. In the primary embodiment disclosed in Bregman, the balloon is controlled to maintain sufficient pressure at the aortic root during diastole to ensure sufficient blood perfusion to the coronary arteries. In an alternative embodiment, a low resistance outlet from the aorta to the inferior vena cava is provided to reduce the aortic pressure during systole, thus, reducing the hemodynamic load on the left ventricle.

Other devices, such as that shown in U.S. Pat. No. 4,034,742 to Thoma, depend upon interaction and coordination with a mechanical pumping chamber containing a movable pumping diaphragm. These devices are intended primarily for application proximate the heart and within the patient's thorax, requiring major invasive surgery.

Many CHF devices are acutely used in the perioperative period. For example, U.S. Pat. No. 4,995,857 to Arnold discloses a perioperative device to pump blood at essentially cardiac rates during surgery when the heart has failed or has been stopped to perform cardiac surgery. The Arnold system temporarily replaces the patient's heart and lung temporarily and pumps blood at cardiac rates, typically 5 to 6 liters/min. Like all systems that bypass the heart and the lungs, an oxygenator is required. Of course, with any system that includes an oxygenator, such as the conventional heart-lung machine, the patient cannot be ambulatory.

With early IABP devices, a polyurethane balloon was mounted on a vascular catheter, inserted into the femoral artery, and positioned in the descending aorta just distal to the left subclavian artery. The balloon catheter was connected to a pump console that pumped helium or carbon dioxide into the balloon during diastole to inflate it. During isovolumic contraction, i.e., during the brief time that the aortic valve is closed and the left ventricle continues to contract, the gas used to actuate the balloon was rapidly withdrawn to deflate the balloon. This reduced the pressure at the aortic root when the aortic valve opened. In contrast, during diastole, the balloon was inflated, causing the diastolic pressure to rise and pushing the blood in the aorta distally towards the lower part of the body (on one side of the balloon) and proximally toward the heart and into the coronary arteries (on the other).

The major advantage in such a counterpulsation device was systolic deflation, which lowered the intra-aortic volume and pressure, reducing both afterload and myocardial oxygen consumption. In other words, when the balloon is inflated, it creates an artificially higher pressure in the aorta, which has the ancillary benefit of greater perfusion through the coronary arteries. When the balloon deflates, just before the aortic valve opens, the pressure and volume of the aorta decrease, relieving some of the hemodynamic burden on the heart. These physiologic responses improved the patient's cardiac output and coronary circulation, temporarily improving hemodynamics. In general, counterpulsation with an IABP can augment cardiac output by about 15%, this being frequently sufficient to stabilize the patient's hemodynamic status, which might otherwise rapidly deteriorate. When there is evidence of more efficient pumping ability by the heart, and the patient has moved to an improved class of hemodynamic status, counterpulsation can be discontinued, by slowly weaning while monitoring for deterioration.

Until 1979, all IABP catheters were inserted via surgical cutdown, generally of the femoral artery. Since then, the development of a percutaneous IABP catheter has allowed quicker, and perhaps safer, insertion and has resulted in more expeditious institution of therapy and expansion of clinical applications. Inflation and deflation of the balloon, however, requires a pneumatic pump that is sufficiently large that it must be employed extracorporeally, thereby restricting the patient's movements and ability to carry out normal, daily activities. IABP devices are, thus, limited to short term use, on the order of a few days to a few weeks.

As discussed above, a variety of ventricular assist pumping mechanisms have been designed. Typically associated with LVADs are valves that are used in the inlet and outlet conduits to insure unidirectional blood flow. Given the close proximity of the heart, unidirectional flow was necessary to avoid inadvertent backflow into the heart. The use of such valves also minimized the thrombogenic potential of the LVAD device.

Typically, the pump associated with older LVADs was a bulky pulsatile flow pump, of the pusher plate or diaphragm style, such as those manufactured by Baxtor Novacor or TCI, respectively. Given that the pump was implanted within the chest and/or abdominal cavity, major invasive surgery was required. The pumps were typically driven through a percutaneous driveline by a portable external console that monitors and reprograms functions.

Alternatively, rotary pumps, such as centrifugal or axial pumps, have been used in heart assist systems. With centrifugal pumps, the blood enters and exits the pump practically in the same plane. An axial pump, in contrast, directs the blood along the axis of rotation of the rotor. Inspired by the Archimedes screw, one design of an axial pump has been miniaturized to about the size of a pencil eraser, although other designs are larger. Despite its small size, an axial pump may be sufficiently powerful to produce flows that approach those used with older LVADs. Even with miniaturized pumps, however, the pump is typically introduced into the left ventricle through the aortic valve or through the apex of the heart, and its function must be controlled from a console outside the body through percutaneous lines.

All of these heart assist systems referred to above serve one or both of two objectives: (1) to improve the performance of a patient's operative-but-diseased heart from the minimum, classified as NYHAC Class IV, to practically normal, classified as I or 0; or (2) to supplement oxygenated blood circulation through the patient to satisfy organ demand when the patient's heart is suffering from CHF. With such systems, extreme pumping and large amounts of energy, volume, and heat dissipation are required.

Many of these heart assist systems have several general features in common: 1) the devices are cardiac in nature; i.e., they are placed directly within or adjacent to the heart, or within one of the primary vessels associated with the heart (aorta), and are often attached to the heart and/or aorta; 2) the devices attempt to reproduce pulsatile blood flow naturally found in the mammillary circulatory system and, therefore, require valves to prevent backflow; 3) the devices are driven from external consoles, often triggered by the electrocardiogram of the patient; and 4) the size of the blood pump, including its associated connectors and accessories, is generally unmanageable within the anatomy and physiology of the recipient. Due to having one or more of these features, the prior art heart assist devices are limited in their effectiveness and/or practicality. It would be advantageous to employ a heart assist system that avoids major invasive surgery and also avoids the use of peripheral equipment that severely restricts a patient's movement.

SUMMARY OF THE INVENTION

The object of the present invention is to address the aspect of CHF that results from altered pump function and abnormal circulatory dynamics while overcoming the limitations of prior art heart assist systems. Without functioning as a bypass to one or more of a patient's organs, the present invention comprises an extracardiac pumping system for supplementing the circulation of blood through the patient without any component thereof being connected to the patient's heart or primary vessel. Thus, it is extracardiac in nature. With the ability to be applied within a minimally invasive procedure, the present invention significantly improves the condition of the patient suffering from CHF, resulting in the patient feeling much better, even where CHF continues. An ancillary but important benefit of the present invention is the ability to apply the present invention in such a way as to also reduce the pumping load on the heart, thereby potentially permitting the heart to recover during use. With the present invention, no bulky pump, valves or oxygenator are required, and no thoracic invasion with major cardiac surgery is required. Indeed, a significant advantage of the present invention is its simplicity while achieving extraordinary results in improving the condition of a patient suffering from CHF.

The extracardiac system of the present invention preferably comprises a rotary pump configured to pump blood through the patient at subcardiac rates; i.e., at a flow rate significantly below that of the patient's heart. Other types of pumps may be effective as well. Pumping the blood tends to revitalize the blood to a certain extent by imparting kinetic and potential energy to the blood discharged from the pump. Importantly, the preferred pump for the present invention pumping system is one that requires a relatively low amount of energy input, when compared to prior art pumps designed to pump at cardiac rates. The pump may be implanted or not, depending upon the capability, practicality, or need of the patient to be ambulatory.

The present system also comprises an inflow conduit fluidly coupled to the pump, to direct blood to the pump from a first peripheral blood vessel, and an outflow conduit fluidly coupled to the pump, to direct blood from the pump to a second peripheral blood vessel. The connection of the inflow and outflow conduits to the blood vessels is performed subcutaneously; not so deep as to involve major invasive surgery. In other words, minimally subdermal. This permits application of the connections in a minimally-invasive procedure. Preferably, the connections to the blood vessels are just below the skin or just below the first layer of muscle, depending upon the blood vessels at issue or the location of the connection, although slightly deeper penetrations may be necessary for some patients.

In one embodiment of the extracardiac system, the pump is a continuous flow and/or pulsatile pump that is implantable and is used to connect two peripheral arteries, such as the femoral artery at the inflow and the left axillary artery at the outflow, although other peripheral blood vessels are contemplated, including other arteries and/or veins, as well as any singular and/or cumulative combination thereof. An alternative embodiment employs a rotary pump that is controllable in a synchronous copulsating or counterpulsating fashion, or in some out-of-phase intermediate thereof. In one application, it is contemplated that the present invention may be applied such that the heart experiences a reduced pressure at the aortic root during systole, thus reducing the hemodynamic burden on the heart and, thus, permitting the heart to recover.

It is contemplated that, where the entire system of the present invention is implanted, that it be implanted subcutaneously without the need for major invasive surgery and, preferably, extrathoracically. For example, the pump may be implanted in the groin area, with the inflow conduit attached to the femoral or iliac artery proximate thereto and the outflow conduit attached to the axillary artery proximate the shoulder. It is contemplated that the outflow conduit be applied by tunnelling it under the skin from the pump to the axillary artery. Where implanted, the pump is preferably powered by an implantable battery that may be recharged externally by an RF induction system or replaced periodically.

The present invention also comprises a method for supplementing the circulation of blood in the patient and potentially reducing the pumping load on the heart of a patient without connecting any component to the patient's heart. The inventive method comprises the steps of implanting a pump configured to pump blood at volumetric rates that are on average subcardiac, wherein the pump has an inflow and outflow conduit attached thereto; connecting a distal end of the inflow conduit to the first peripheral blood vessel with a minimally-invasive surgical procedure to permit the flow of blood to the pump from a first peripheral blood vessel of the patient; implanting the inflow conduit subcutaneously; connecting a distal end of the outflow conduit to the second peripheral blood vessel with a minimally-invasive surgical procedure to permit the flow of blood away from the pump to a second peripheral blood vessel of the patient; and operating said pump to perfuse blood through the patient's circulatory system. In one specific application, the pump is capable of synchronous control wherein the step of operating the pump includes the steps of beginning discharge of blood out of the pump during isovolumic contraction and discontinuing discharge of blood when the aortic valve closes following systole. Depending upon the patient and the specific arrangement of the present system, this specific method results in reduced after-load on the heart while also supplementing circulation. For example, in one embodiment, the first and second blood vessels are the femoral and axillary arteries, respectively.

In an alternative method of applying the present invention, the pump is not implanted and the inflow and outflow conduits are connected to the first and second blood vessels percutaneously, using a readily-removable connector, such as a cannula, to connect the distal ends of each conduit to the blood vessels.

An important advantage of the present invention is that it utilizes the benefits of an IABP, without the requirement of extracorporeal equipment or the need to have a balloon or similar implement partially obstructing a blood vessel. The present invention thus offers simplicity and long-term use.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENTS

Turning now to the drawings provided herein, a more detailed description of the embodiments of the present invention is provided below. It should be noted, however, that while some embodiments have all of the advantages identified herein, other embodiments may only realize some but not all of the advantages.

The present invention provides a heart assist system that is extracardiac in nature. In other words, the present invention supplements blood perfusion, without the need to interface directly with the heart and aorta. Thus, no major invasive surgery is necessary to use the present invention. In some circumstances, the present invention also lessens the hemodynamic burden on the heart by reducing the pressure at the aortic root during systole.

Figure 2:
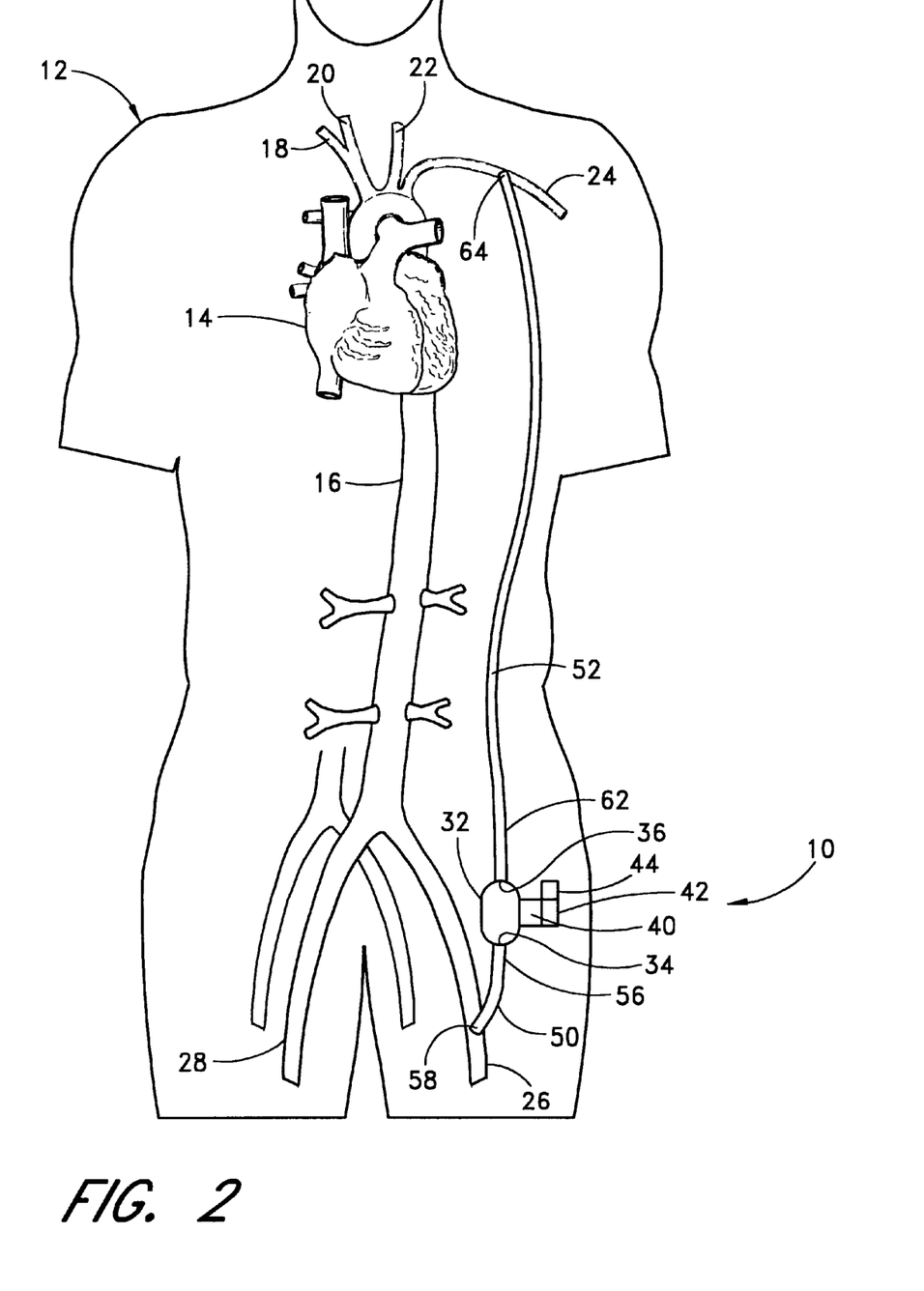
FIG. 2 is a schematic view of a first embodiment of the present invention, shown applied to a patient's circulatory system.

With reference to FIG. 2, a first embodiment of the present invention 10 is shown applied to a patient 12 having an ailing heart 14 and an aorta 16, from which peripheral brachiocephalic blood vessels extend, including the right subclavian 18, the right carotid 20, the left carotid 22, and the left axillary 24. Extending from the descending aorta is another set of peripheral blood vessels, the left and right femoral arteries 26, 28.

The first embodiment 10 comprises a pump 32 having an inlet 34 and an outlet 36 for connection of flexible conduits thereto. The pump 32 is preferably a rotary pump, either an axial type or a centrifugal type, although other types of pumps may be used, whether commercially-available or customized. In either case, the pump should be sufficiently small to be implanted subcutaneously and preferably extrathoracically, for example in the groin area of the patient, without the need for major invasive surgery. Because the present invention is an extracardiac system, no valves are necessary. Any inadvertent backflow through the pump and/or through the inflow conduit would not harm the patient.

Regardless of the style chosen, the pump 32 of the present invention is sized to pump blood at subcardiac volumetric rates, less than about 50% of the flow rate of an average healthy heart, although flow rates above that may be effective. Thus, the pump 32 of the present invention is sized and configured to discharge blood at volumetric flow rates anywhere in the range of 0.1 to 3 liters per minute, depending upon the application desired and/or the degree of need for heart assist. For example, for a patient experiencing advanced congestive heart failure, it may be preferable to employ a pump that has an average subcardiac rate of 2.5 to 3 liters per minute. In other patients, particularly those with minimal levels of heart failure, it may be preferable to employ a pump that has an average subcardiac rate of 0.5 liters per minute or less.

In one embodiment, the pump selected is a continuous flow pump so that blood perfusion through the circulation system is continuous. In an alternative embodiment, the pump selected has the capability of synchronous actuation; i.e., it may be actuated in a pulsatile mode, either in copulsating or counterpulsating fashion.

For copulsating action, it is contemplated that the pump 32 would be actuated to discharge blood generally during systole, beginning actuation, for example, during isovolumic contraction before the aortic valve opens or as the aortic valve opens. The pump would be static while the aortic valve is closed following systole, ceasing actuation, for example, when the aortic valve closes.

For counterpulsating actuation, it is contemplated that the pump 32 would be actuated generally during diastole, ceasing actuation, for example, before or during isovolumic contraction. Such an application would permit and/or enhance coronary blood perfusion. In this application, it is contemplated that the pump would be static during the balance of systole after the aortic valve is opened, to lessen the burden against which the heart must pump. The aortic valve being open encompasses the periods of opening and closing, wherein blood is flowing therethrough.

It should be recognized that the designations copulsating and counterpulsating are general identifiers and are not limited to specific points in the patient's heart cycle when the pump begins and discontinues actuation. Rather, they are intended to generally refer to pump actuation in which the pump is actuating, at least in part, during systole and diastole, respectively. For example, it is contemplated that the pump might be activated to be out of phase from true copulsating or counterpulsating actuation described herein, and still be synchronous, depending upon the specific needs of the patient or the desired outcome. One might shift actuation of the pump to begin prior to or after isovolumic contraction or to begin before or after isovolumic expansion.

Furthermore, the pulsatile pump may be actuated to pulsate asynchronously with the patient's heart. Typically, where the patient's heart is beating irregularly, there may be a desire to pulsate the pump asynchronously so that the perfusion of blood by the extracardiac pumping system is more regular and, thus, more effective at oxygenating the organs. Where the patient's heart beats regularly, but weakly, synchronous pulsation of the extracardiac pump may be preferred.

The pump 32 is driven by an electric motor 40 and is controlled preferably by a programmable controller 42 that is capable of actuating the pump in pulsatile fashion, where desired, and also of controlling the speed of the pump. For synchronous control, the patient's heart would preferably be monitored with an EKG in which feedback would be provided the controller 42. The controller 42 is preferably programmed by the use of external means. This may be accomplished, for example, using RF telemetry circuits of the type commonly used within implantable pacemakers and defibrillators. The controller may also be autoregulating to permit automatic regulation of the speed, and/or regulation of the synchronous or a synchronous pulsation of the pump, based upon feedback from ambient sensors monitoring parameters, such as pressure or the patient's EKG. It is also contemplated that a reverse-direction pump be utilized, if desired, in which the controller is capable of reversing the direction of either the motor or the impellers of the pump. Such a pump might be used where it is desirable to have the option of reversing the direction of circulation between two peripheral blood vessels.

Power to the motor 40 and controller 42 is provided by a battery 44 that is preferably rechargeable by an external induction source (not shown), such as an RF induction coil that may be electromagnetically coupled to the battery to induce a charge therein. The pump can be temporarily stopped during recharging with no appreciable life threatening effect, because the system only supplements the heart, rather than substituting for the heart.

While the controller 42 and battery 44 are preferably pre-assembled to the pump 32 and implanted therewith, it is also contemplated that the pump 32 and motor 40 be implanted at one location and the controller 42 and battery 44 be implanted in a separate location. In one alternative arrangement, the pump 32 may be driven externally through a percutaneous drive line. In another alternative, the pump, motor and controller may be implanted and powered by an extracorporeal battery. In the latter case, the battery could be attached to the side of the patient to permit fully ambulatory movement.

The inlet 34 of the pump 32 is preferably connected to a flexible inflow conduit 50 and a flexible outflow conduit 52 to direct blood flow from one peripheral blood vessel to another. The inflow and outflow conduits 50, 52 may, for example, be formed from Dacron, Hemashield or Gortex materials, although other materials may be suitable. In some cases, the inflow and/or outflow conduits may come commercially already attached to the pump. Where it is desired to implant the pump 32 and the conduits 50, 52, it is preferably that the inner diameter of the conduits be less than 25 mm, although diameters slightly larger may be effective.

In one preferred application of the present invention, the first embodiment is applied in an arterial-arterial fashion; for example, as a femoral-axillary bypass, as is shown in FIG. 2. It should be appreciated by one of ordinary skill in the art that an axillary-femoral bypass would also be effective using the embodiments described herein. Indeed, it should be recognized by one of ordinary skill in the art that the present invention might be applied to any of the peripheral blood vessels in the patient.

The inflow conduit 50 has a first proximal end 56 that connects with the inlet 34 of the pump 32 and a second distal end 58 that connects with a first peripheral blood vessel, which is preferably the left femoral artery 26 of the patient 12, although the right femoral artery or any other peripheral artery may be acceptable. In one application, the connection between the inflow conduit 50 and the first blood vessel is via an end-to-side anastomosis, although a side-to-side anastomosis connection might be used mid-stream of the conduit where the inflow conduit were connected at its second end to an additional blood vessel (not shown).

Similarly, the outflow conduit 52 has a first proximal end 62 that connects to the outlet 36 of the pump 32 and a second distal end 64 that connects with a second peripheral blood vessel, preferably the left axillary artery 24 of the patient 12, although the right axillary artery, or any other peripheral artery, would be acceptable. In one application, the connection between the outflow conduit 52 and the second blood vessel is via an end-to-side anastomosis, although a side-to-side anastomosis connection might be used mid-stream of the conduit where the outflow conduit were connected at its second end to yet another blood vessel (not shown). Preferably, the outflow conduit is attached to the second blood vessel at an angle that results in the predominant flow of blood out of the pump proximally toward the aorta and heart, such as is shown in FIG. 2.

It is preferred that application of the present invention to the peripheral blood vessels be accomplished subcutaneously; i.e., at a shallow depth just below the skin or first muscle layer so as to avoid major invasive surgery. It is also preferred that the present invention be applied extrathoracically to avoid the need to invade the patient's chest cavity.

Where desired, the entire extracardiac system of the present invention 10 may be implanted within the patient 12. In that case, the pump 32 may be implanted, for example, into the groin area, with the inflow conduit 50 connected subcutaneously to, for example, the femoral artery 26 proximate the pump 32. The outflow conduit would be tunnelled subcutaneously through to, for example, the left axillary artery 24. In an alternative arrangement, the pump 32 and associated drive and controller could be temporarily fastened to the exterior skin of the patient, with the inflow and outflow conduits 50, 52 connected percutaneously. In either case, the patient may be ambulatory without restriction of tethered lines.

Figure 3:
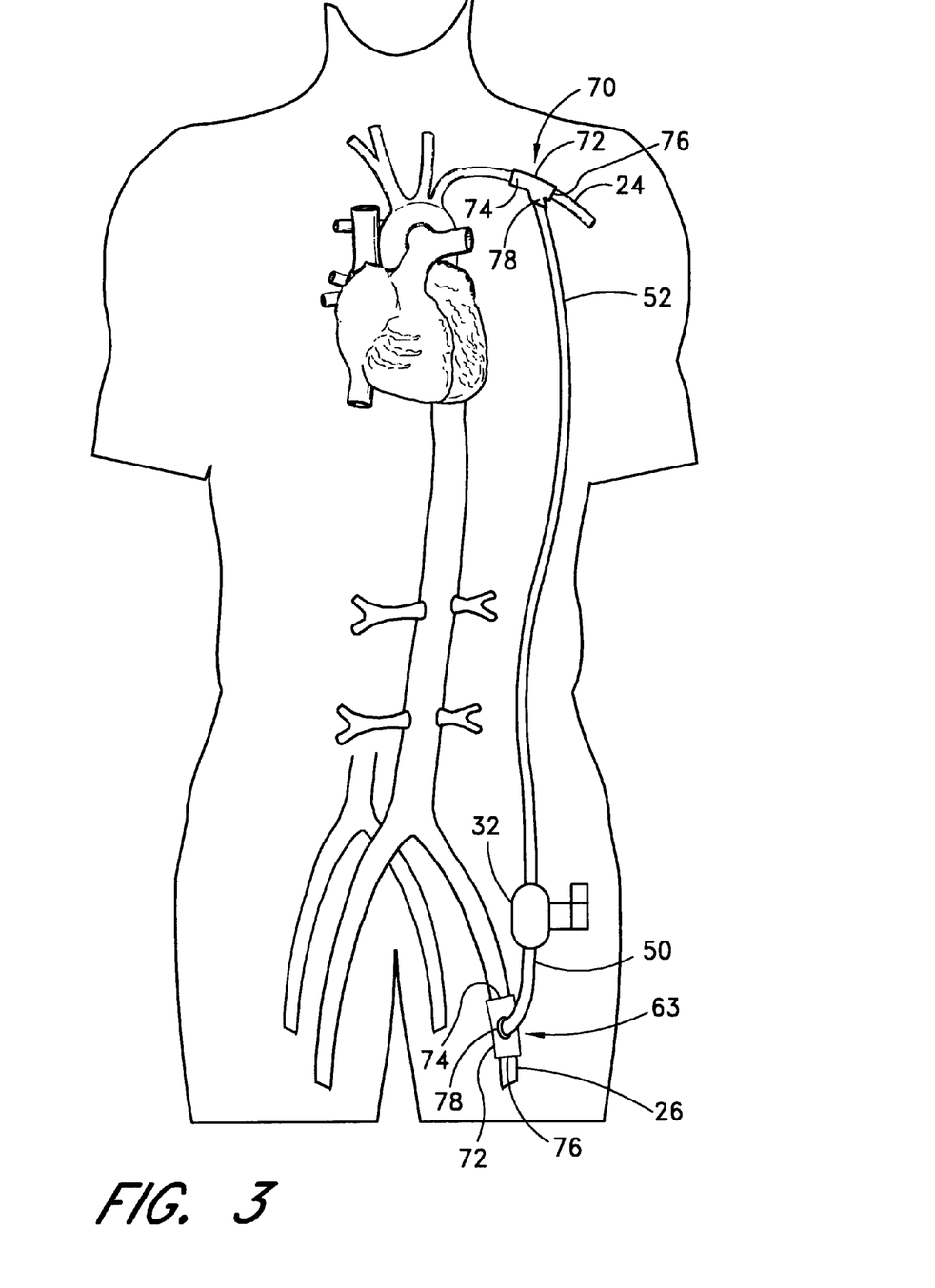
FIG. 3 is a schematic view of a second embodiment of the present invention, shown applied to a patient's circulatory system.

It is contemplated that, where an anastomosis connection is not desired, a special connector may be used to connect the conduits 50, 52 to the peripheral blood vessels. With reference to FIG. 3, a second embodiment of the present invention is shown, wherein the inflow conduit 50 and outflow conduit 52 are connected to the peripheral blood vessels via first and second connectors 68, 70 each comprising three-opening fittings. In the preferred embodiment, the connectors 68, 70 comprise an intra-vascular, generally-tee-shaped fitting 72 having a proximal end 74, a distal end 76, and an angled divergence 78 permitting connection to the inflow and outflow conduits 50, 52 and the blood vessels. The proximal and distal ends 74, 76 of the fittings 72 permit connection to the blood vessel into which the fitting is positioned. The angle of the divergence 78 of the fittings 72 may be 90 degrees or less from the axis of flow through the blood vessel. In another embodiment, the connectors 68, 70 are sleeves (not shown) that surround and attach to the outside of the peripheral blood vessel where, within the interior of the sleeve, a port to the blood vessel is provided to permit blood flow from the conduits 50, 52 when they are connected to the connectors 68, 70, respectively. Other types of connectors having other configurations are contemplated that may avoid the need for an anastomosis connection or that permit connection of the conduits to the blood vessels. It is contemplated that a connection to the blood vessels might be made via a cannula, wherein the cannula is implanted, along with the inflow and outflow conduits.

The advantage of discrete connectors is their potential application to patients with chronic CHF. A connector eliminates a need for an anastomosis connection between the conduits of the present invention system and the peripheral blood vessels where it is desired to remove and/or replace the system more than one time. The connectors could be applied to the first and second blood vessels semipermanently, with an end cap applied to the divergence for later quick-connection of the present invention system to the patient. In this regard, a patient might experience the benefit of the present invention periodically, without having to reconnect and redisconnect the conduits from the blood vessels via an anastomosis procedure each time. Each time it is desired to implement the present invention, the end caps would be removed and the conduit attached to the connectors quickly.

In the preferred embodiment of the connector 70, the divergence 78 is oriented at an acute angle significantly less than 90° from the axis of the fitting 72, as shown in FIG. 3, so that a majority of the blood flowing through the outflow conduit 52 into the blood vessel (e.g., left axillary 24) flows in a direction proximally toward the heart 14, rather than in the distal direction. In an alternative embodiment, the proximal end 74 of the fitting 72 may have a diameter larger than the diameter of the distal end 76, without need of having an angled divergence, to achieve the same result.

With or without a connector, with blood flow directed proximally toward the aorta, the result may be concurrent flow down the descending aorta, which will result in the reduction of pressure at the aortic root. Thus, the present invention may be applied so to reduce the afterload on the patient's heart, permitting at least partial if not complete CHF recovery, while supplementing blood circulation. Concurrent flow depends upon the phase of operation of the pulsatile pump and the choice of second blood vessel to which the outflow conduit is connected.

Figure 4:
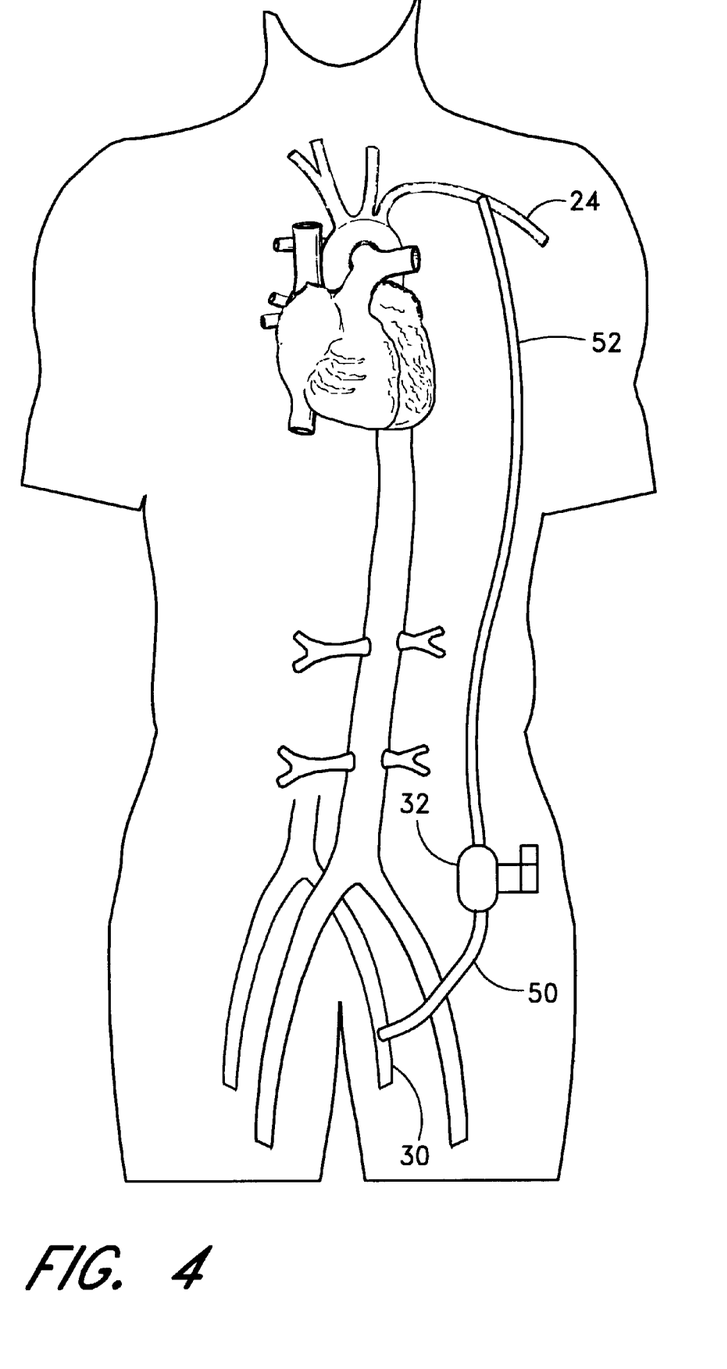
FIG. 4 is a schematic view of a variation of the first embodiment of FIG. 2 shown implanted into a patient.

While the present invention may be applied to create an arterial-arterial bypass, given the nature of the present invention, i.e., supplementation of circulation to meet organ demand, a venous-arterial bypass may also be used. For example, with reference to FIG. 4, one embodiment of the present invention 10 may be applied to the patient 12 such that the inflow conduit 50 is connected to a peripheral vein, such as the left femoral vein 80. In this arrangement, the outflow conduit 50 may be connected to one of the peripheral arteries, such as the left axillary 24. Arterial-venous arrangements are contemplated as well. In those venous-arterial cases where the inflow is connected to a vein and the outflow is connected to an artery, the pump 32 should be sized to permit flow sufficiently small so that oxygen-deficient blood does not rise to unacceptable levels in the arteries. It should be appreciated that the connections to the peripheral veins could be by one or more methods described above for connecting to a peripheral artery. It should also be appreciated that the present invention could be applied as a venous-venous bypass, wherein the inflow and outflow are connected to separate peripheral veins. In addition, an alternative embodiment comprises two discrete pumps and conduit arrangements, one being applied as a venous-venous bypass, and the other as an arterial-arterial bypass.

Figure 5:
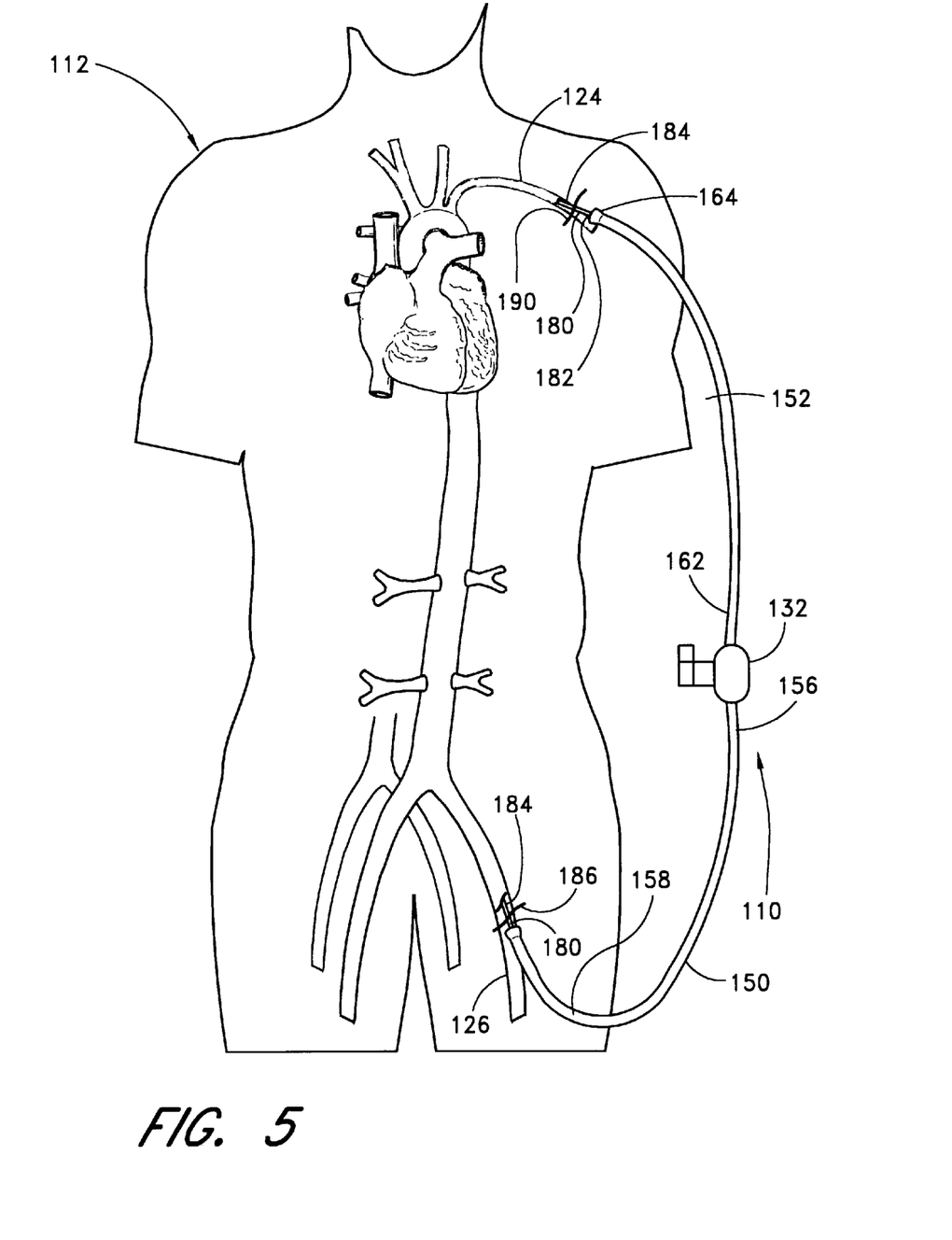
FIG. 5 is a schematic view of a third embodiment of the present invention, shown applied to a patient's circulatory system.

A partial external application of the present invention is contemplated where a patient's heart failure is acute; i.e., is not expected to last long, or in the earlier stages of heart failure (where the patient is in New York Heart Association Classification (NYHAC) functional classes II or III). With reference to FIG. 5, a third embodiment of the present invention 110 is applied percutaneously to a patient 112 to bypass between two peripheral blood vessels wherein a pump 132 and its associated motor and controls are employed extracorporeally. The pump 132 has an inflow conduit 150 and an outflow conduit 152 associated therewith for connection to two peripheral blood vessels. The inflow conduit 150 has a first end 156 and second end 158 wherein the second end is connected to a first peripheral blood vessel (e.g., femoral artery 126) by way of a cannula 180. The cannula 180 has a first end 182 sealably connected to the second end 158 of the inflow conduit 150. The cannula 180 also has a second end 184 used to pierce the skin or first layer of muscle through surgical opening 186 and to pierce the blood vessel source (e.g., femoral artery 126).

Similarly, the outflow conduit 152 has a first end 162 and second end 164 wherein the second end is connected to a second peripheral blood vessel (e.g., left axillary artery 124) by way of a cannula 180. Like the inflow cannula, the outflow cannula 180 has a first end 182 sealably connected to the second end 164 of the outflow conduit 152. The outflow cannula 180 also has a second end 184 used to pierce the skin or first layer of muscle through surgical opening 190 and to pierce the second blood vessel (e.g., left axillary artery 124). By use of a percutaneous application, the present invention may be applied temporarily without the need to implant any aspect thereof or to make anastomosis connections to the blood vessels.

An alternative variation of the third embodiment may be used where it is desired to treat a patient periodically, but for short periods of time each occasion and without the use of special connectors. With this variation, it is contemplated that the second ends of the inflow and outflow conduits be more permanently connected to the associated blood vessels via, for example, an anastomosis connection, wherein a portion of each conduit proximate to the blood vessel connection is implanted percutaneously with a removable cap enclosing the externally-exposed first end (or an intervening end thereof) of the conduit external to the patient. When it is desired to provide a circulatory bypass to supplement blood flow, the removable cap on each exposed percutaneously-positioned conduit could be removed and the pump (or the pump with a length of inflow and/or outflow conduit attached thereto) inserted between the exposed percutaneous conduits. In this regard, a patient may experience the benefit of the present invention periodically, without having to reconnect and redisconnect the conduits from the blood vessels each time.

Figure 6:
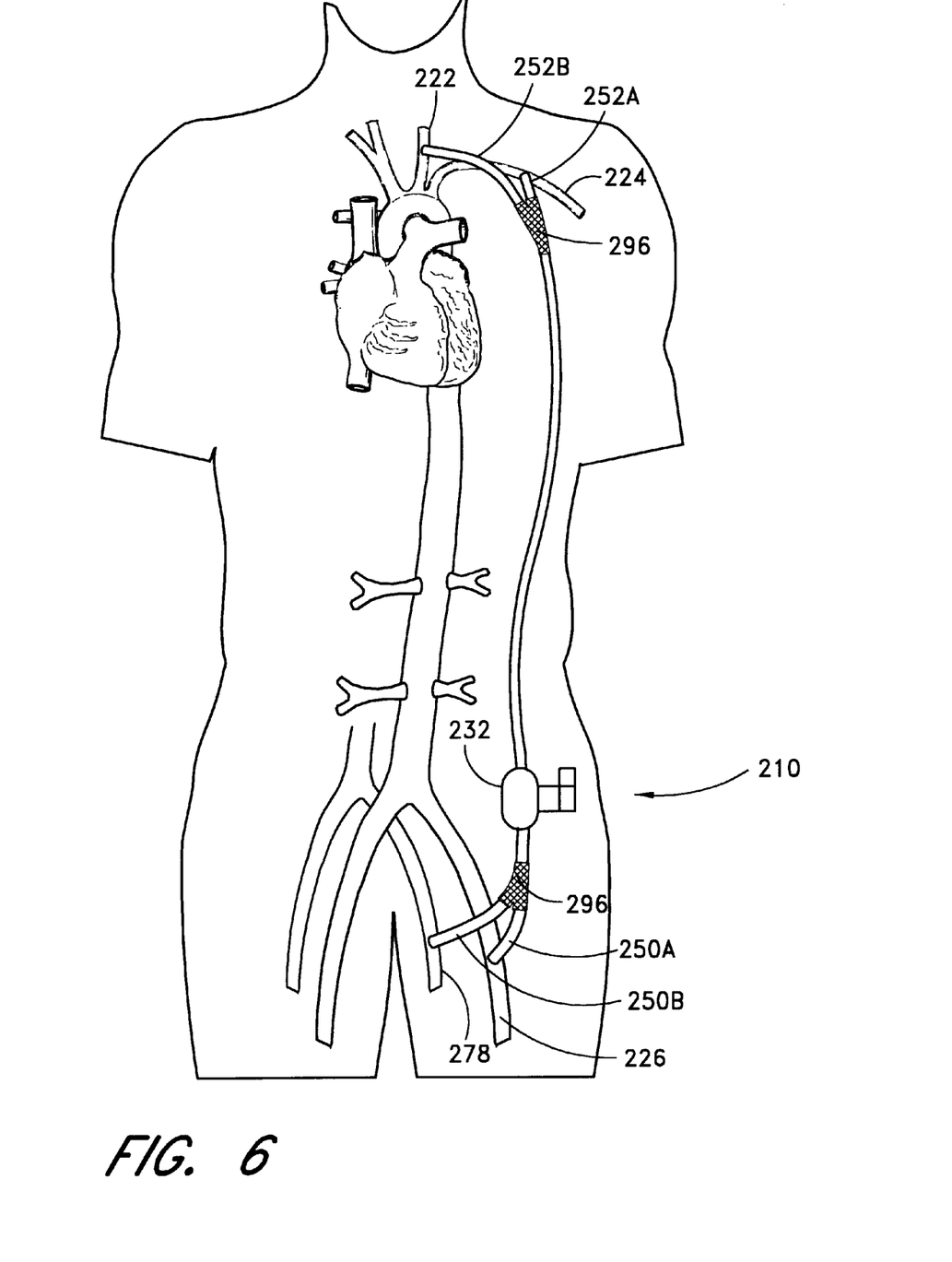
FIG. 6 is a schematic view of a fourth embodiment of the present invention, shown applied to a patient's circulatory system.

Another embodiment of the present invention includes a plurality of inflow and/or outflow conduits. For example, with reference to FIG. 6, a fourth embodiment of the present invention 210 includes a pump 232 in fluid communication with a plurality of inflow conduits 250A, 250B and a plurality of outflow conduits 252A, 252B. Each pair of conduits converges at a generally Y-shaped convergence 296 that converges the flow at the inflow end and diverges the flow at the outflow end. Each conduit may be connected to a separate peripheral blood vessel, although it is possible to have two connections to the same blood vessel at remote locations. In one arrangement, all four conduits are connected to peripheral arteries. Alternatively, one or more of the conduits could be connected to veins. In the application shown in FIG. 6, inflow conduit 250A is connected to left femoral artery 226 while inflow conduit 250B is connected to left femoral vein 278. Outflow conduit 252A is connected to left axillary artery 224 while outflow conduit 252B is connected to left carotid artery 222. It should be noted that the connections of any or all of the conduits to the blood vessels may be via an anastomosis connection or via a special connector, as described above. In addition, the embodiment of FIG. 6 may be applied to any combination of peripheral blood vessels that would best suit the patient's condition. For example, it may be desired to have one inflow conduit and two outflow conduits or vice versa. Finally, it should be noted that more than two conduits may be used on the inflow or outflow side, where the number of inflow conduits is not necessarily equal to the number of outflow conduits.

While the above description has explained the inventive features of the invention as applied to various embodiments, it will be understood that the variations in the form and details of the apparatus or method may be made by those of ordinary skill in the art without departing from the spirit of the invention. The scope of the invention is indicated by the appended claims herein, however, not by the foregoing description.

What is claimed is:

1. An extracardiac pumping system for supplementing blood circulation through a patient experiencing congestive heart failure without any component thereof being connected to the patient's heart, the extracardiac system comprising:

a pump configured to pump blood through the patient at subcardiac volumetric rates, said pump having an average flow rate that, during normal operation thereof, is substantially below that of the patient's heart when healthy;

an inflow conduit fluidly coupled to the pump to direct blood to the pump from a first peripheral blood vessel, the inflow conduit having a first end sized and configured to couple to the first peripheral blood vessel;

an outflow conduit fluidly coupled to the pump to direct blood from the pump to a second peripheral blood vessel, the outflow conduit having a first end sized and configured to couple to the second peripheral blood vessel; and at least one additional outflow conduit having a first end configured to connect to a peripheral blood vessel;

whereby connection of the first ends of the inflow and outflow conduits to the blood vessels may be made subcutaneously to permit application of the connections in an minimally-invasive procedure.

2. An extracardiac pumping system for supplementing blood circulation through a patient experiencing congestive heart failure without any component thereof being connected to the patient's heart, the extracardiac system comprising:

a pulsatile pump configured to pump blood through the patient at subcardiac volumetric rates, said pump having an average flow rate that, during normal operation thereof, is substantially below that of the patient's heart when healthy;

an inflow conduit fluidly coupled to the pump to direct blood to the pump from a first peripheral blood vessel, the inflow conduit having a first end sized and configured to couple to the first peripheral blood vessel; and, an outflow conduit fluidly coupled to the pump to direct blood from the pump to a second peripheral blood vessel, the outflow conduit having a first end sized and configured to couple to the second peripheral blood vessel; and a control circuit to synchronously actuate the pump so as to begin pumping during isovolumic contraction and discontinue pumping about when the aortic valve closes;

whereby connection of the first ends of the inflow and outflow conduits to the blood vessels may be made subcutaneously to permit application of the connections in an minimally-invasive procedure.

3. An extracardiac pumping system for supplementing blood circulation through a patient experiencing congestive heart failure without any component thereof being connected to the patient's heart, the extracardiac system comprising:

a pump configured to pump blood through the patient at subcardiac volumetric rates, said pump having an average flow rate that, during normal operation thereof, is substantially below that of the patient's heart when healthy;

an inflow conduit fluidly coupled to the pump to direct blood to the pump from a first peripheral blood vessel, the inflow conduit having a first end sized and configured to couple to the first peripheral blood vessel; and, an outflow conduit fluidly coupled to the pump to direct blood from the pump to a second peripheral blood vessel, the outflow conduit having a first end sized and configured to couple to the second peripheral blood vessel;

wherein the pump, inflow conduit and outflow conduit are sized and configured to be implantable using a minimally-invasive surgical procedure, and whereby connection of the first ends of the inflow and outflow conduits to the blood vessels may be made subcutaneously to permit application of the connections in an minimally-invasive procedure.

4. The extracardiac pumping system of claim 3 further comprising an implantable battery.

5. The extracardiac pumping system of claim 4 further comprising an induction coil configured to electromagnetically couple to the battery for charging the battery following implantation of said battery and pump.

6. An extracardiac pumping system for supplementing blood circulation through a patient experiencing congestive heart failure without any component thereof being connected to the patient's heart, the extracardiac system comprising:

a pump configured to pump blood through the patient at subcardiac volumetric rates, said pump having an average flow rate that, during normal operation thereof, is substantially below that of the patient's heart when healthy;

an inflow conduit comprising flexible tubing having an inner diameter that is less than 25 millimeters fluidly coupled to the pump to direct blood to the pump from a first peripheral blood vessel, the inflow conduit having a first end sized and configured to couple to the first peripheral blood vessel; and, an outflow conduit comprising flexible tubing having an inner diameter that is less than 25 millimeters fluidly coupled to the pump to direct blood from the pump to a second peripheral blood vessel, the outflow conduit having a first end sized and configured to couple to the second peripheral blood vessel;

whereby connection of the first ends of the inflow and outflow conduits to the blood vessels may be made subcutaneously to permit application of the connections in an minimally-invasive procedure.

7. An extracardiac pumping system for supplementing blood circulation through a patient experiencing congestive heart failure without any component thereof being connected to the patient's heart, the extracardiac system comprising:

a pump configured to pump blood through the patient at subcardiac volumetric rates, said pump having an average flow rate that, during normal operation thereof, is substantially below that of the patient's heart when healthy;

an inflow conduit fluidly coupled to the pump to direct blood to the pump from a first peripheral blood vessel, the inflow conduit having a first end sized and configured to couple to the first peripheral blood vessel;

an outflow conduit fluidly coupled to the pump to direct blood from the pump to a second peripheral blood vessel, the outflow conduit having a first end sized and configured to couple to the second peripheral blood vessel; and, a connector for affixing to one of the peripheral blood vessels and for connecting to one of the conduits whereby connection of the first ends of the inflow and outflow conduits to the blood vessels may be made subcutaneously to permit application of the connections in an minimally-invasive procedure.

8. The extracardiac pumping system of claim 7, wherein the connector has a divergence of less than 90 degrees so that a majority of the blood pumped into the peripheral vessel may be directed proximally toward the heart when the system is in use.

9. An extracardiac pumping system configured to supplement the circulation of blood through a patient, the extracardiac system comprising:

an extrathoracic pump adapted to pump blood between peripheral arteries, said pump configured to be implanted extrathoracically and subcutaneously without the use of a major invasive procedure;

a pump inflow conduit connectable to a first peripheral artery; and a pump outflow conduit connectable to a second peripheral artery, said pump outflow conduit configured to connect to the second peripheral in such a way that a majority of the blood pumped therethrough is directed proximally toward the heart, whereby connection of the inflow and outflow conduits to the blood vessels may be subcutaneous to permit application of the connections in an minimally-invasive procedure.

10. The extracardiac pumping system of claim 9, wherein the pump is a continuous flow pump.

11. The extracardiac pumping system of claim 9, wherein the pump is actuated in a pulsatile fashion so as to reduce the hemodynamic burden on the heart.

12. An extracardiac pumping system for reducing the pumping load on the heart of a patient, said extracardiac pump configured to facilitate cardiac recovery by supplementing the circulation of blood through the patient without any component thereof being connected to the patient's heart, the extracardiac system comprising:

a pump configured to pump blood synchronously with the patient's heart within a range of flow rates that, during normal operation thereof, are between 0.1 and 3 liters/min., said pump being implantable at or about the patient's groin in a minimally-invasive procedure;

an implantable battery for providing electrical power to the pump;

a controller for controlling actuation of the pump in a synchronous manner to permit pulsatile blood circulation, said controller being configured so as to be capable of actuation during systole when the aortic valve is open;

means for charging the battery extracorporeally so that the battery may be recharged without the need of a surgical procedure;

an inflow conduit having an inner diameter no greater than 25 mm, the inflow conduit configured to fluidly couple to the pump to direct blood to the pump from a peripheral artery of the patient via a subcutaneous anastomosis connection, and an outflow conduit having an inner diameter no greater than 25 mm, the outflow conduit configured to fluidly couple to the pump to direct blood from the pump to a peripheral artery that stems from the patient's aortic arch via a subcutaneous anastomosis connection.

13. An extracardiac pumping system for supplementing the circulation of blood through a patient without any component thereof being connected to the patient's heart, the extracardiac system comprising:

a rotary pump configured to pump blood continuously at subcardiac rates of less than 3.0 liters/minute;

a controller for controlling actuation of the pump in a continuous manner, said controller permitting variable speed actuation;

an inflow conduit having an inner diameter no greater than 25 mm, the inflow conduit configured to fluidly couple to the pump to direct blood to the pump from a first peripheral blood vessel of the patient via a subcutaneous anastomosis connection, and an outflow conduit having an inner diameter no greater than 25 mm, the outflow conduit configured to fluidly couple to the pump to direct blood from the pump to a second peripheral blood vessel via a subcutaneous anastomosis connection.

14. The extracardiac pumping system of claim 13, wherein said pump is implantable extrathoracically in a minimally-invasive procedure.

15. The extracardiac pumping system of claim 13, further comprising an implantable battery for providing electrical power to the pump, and means for charging the battery extracorporeally so that the battery may be recharged without the need of a surgical procedure.

16. A method for supplementing the circulation of blood through the patient without connecting any component to the patient's heart, the method comprising the steps of:

connecting a distal end of an inflow conduit of a rotary pump to a first peripheral blood vessel via a cannula in a percutaneous application with a minimally invasive surgical procedure to permit the flow of blood to the pump from the first peripheral blood vessel, said rotary pump configured to pump blood at volumetric rates that are on average subcardiac;

connecting a distal end of an outflow conduit of the pump to a second peripheral blood vessel via a cannula in a percutaneous application with a minimally invasive surgical procedure to permit the flow of blood away from the pump to the second peripheral blood vessel; and operating said pump to perfuse blood through the patient's circulatory system.

17. A method for supplementing the circulation of blood through the patient without connecting any component to the patient's heart, the method comprising the steps of:

connecting a distal end of an inflow conduit of a rotary pump to a first peripheral artery with a minimally invasive surgical procedure to permit the flow of blood to the pump from the first peripheral artery, said rotary pump configured to pump blood at volumetric rates that are on average subcardiac;

connecting a distal end of an outflow conduit of the pump to a second peripheral artery with a minimally invasive surgical procedure to permit the flow of blood away from the pump to the second peripheral artery; and operating said pump to perfuse blood through the patient's circulatory system.

18. The method of claim 17, wherein the connection between the distal end of the inflow conduit and the first peripheral blood vessel is made with a cannula.

19. The method of claim 17, wherein the connection between the distal end of the inflow conduit and the first peripheral blood vessel is made with an anastomosis connection.

20. The method of claim 17, wherein the inflow and outflow conduit distal ends are connected to a femoral artery and an axillary artery, respectively.

21. A method for supplementing the circulation of blood through the patient without connecting any component to the patient's heart, the method comprising the steps of:

connecting a distal end of an inflow conduit of a rotary pump to a first peripheral blood vessel with a minimally invasive surgical procedure to permit the flow of blood to the pump from the first peripheral blood vessel, said rotary pump configured to pump blood at volumetric rates that are on average subcardiac;

connecting a distal end of an outflow conduit of the pump to a second peripheral blood vessel with a minimally invasive surgical procedure to permit the flow of blood away from the pump to the second peripheral blood vessel; and operating said pump in copulsating fashion to perfuse blood through the patient's circulatory system.

22. The method of claim 21, wherein the pump is controlled so as to begin actuation during isovolumic contraction.

23. A method for supplementing the circulation of blood through the patient without connecting any component to the patient's heart, the method comprising the steps of:

connecting a distal end of an inflow conduit of a rotary pump to a first peripheral vein with a minimally invasive surgical procedure to permit the flow of blood to the pump from the first peripheral vein, said rotary pump configured to pump blood at volumetric rates that are on average subcardiac;

connecting a distal end of an outflow conduit of the pump to a second peripheral vein with a minimally invasive surgical procedure to permit the flow of blood away from the pump to the second peripheral vein; and operating said pump to perfuse blood through the patient's circulatory system.

24. A method for supplementing the circulation of blood through the patient without connecting any component to the patient's heart, the method comprising the steps of:

connecting a distal end of an inflow conduit of a rotary pump to a first peripheral blood vessel with a minimally invasive surgical procedure to permit the flow of blood to the pump from the first peripheral blood vessel, said rotary pump configured to pump blood at volumetric rates that are on average subcardiac;

connecting a distal end of an outflow conduit of the pump to a second peripheral blood vessel with a minimally invasive surgical procedure to permit the flow of blood away from the pump to the second peripheral blood vessel;

connecting an intervening length of conduit between the distal end of the inflow conduit and the pump; and operating said pump to perfuse blood through the patient's circulatory system.

25. A method for supplementing the circulation of blood through the patient without connecting any component to the patient's heart, the method comprising the steps of:

connecting a distal end of an inflow conduit of a rotary pump to a first peripheral blood vessel with a minimally invasive surgical procedure to permit the flow of blood to the pump from the first peripheral blood vessel, said rotary pump configured to pump blood at volumetric rates that are on average subcardiac;

connecting a distal end of an outflow conduit of the pump to a second peripheral blood vessel with a minimally invasive surgical procedure to permit the flow of blood away from the pump to the second peripheral blood vessel;

connecting an intervening length of conduit between the distal end of the outflow conduit and the pump; and operating said pump to perfuse blood through the patient's circulatory system.

* * * * *